United States Patent
Kadurugamuwa et al.

(10) Patent No.: US 7,674,602 B2
(45) Date of Patent: Mar. 9, 2010

(54) METHOD FOR DETECTING A PLURALITY OF CATALASE POSITIVE MICROORGANISMS

(75) Inventors: Jagath Kadurugamuwa, Pleasanton, CA (US); William L. Smith, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 123 days.

(21) Appl. No.: 12/034,340

(22) Filed: Feb. 20, 2008

(65) Prior Publication Data

US 2009/0208996 A1     Aug. 20, 2009

(51) Int. Cl.
*C12Q 1/22*     (2006.01)
(52) U.S. Cl. ........................................ 435/31
(58) Field of Classification Search .................... 435/31, 435/27; 422/28
See application file for complete search history.

(56) References Cited

U.S. PATENT DOCUMENTS

| | | | | |
|---|---|---|---|---|
| 7,403,805 | B2 * | 7/2008 | Abreu | 600/318 |
| 2005/0283045 | A1 | 12/2005 | Yamamoto et al. | |
| 2007/0154466 | A1 | 7/2007 | Weber et al. | |
| 2009/0158848 | A1 * | 6/2009 | Brooks et al. | 73/579 |

FOREIGN PATENT DOCUMENTS

| | | |
|---|---|---|
| EP | 223479 | 5/1987 |
| EP | 436466 | 7/1991 |
| EP | 486653 | 5/1996 |

OTHER PUBLICATIONS

Dickert F. et al. Sensor Strategies for Microorganism Detection. Anal Bioanal Chem 377:540-549, 2003.*
Leonard P. et al. Advances in Biosensors for Detection of Pathogens in Food and Water. Enzyme and Microbial Tech 32:3-13, 2003.*
Deng L. et al. Continuous Measurement of Bacterial Populations on the Surface of a Solid Medium with a Thickness Shear Mode Acoustic Resonator in Series. Enzyme and Microbial Tech 19(7)525-528, 1996.*
Jyoti K. et al. Hybrid Cavitation Methods for Water Disinfection. Biochemical Engineering J 14(1)9-17, 2003.*

* cited by examiner

*Primary Examiner*—Ralph Gitomer
(74) *Attorney, Agent, or Firm*—Alok Goel

(57) ABSTRACT

This invention is directed to a method and kit for detecting microorganisms on a surface. The invention involves contacting a household surface with a cleaning composition comprising hydrogen peroxide and then placing an acoustic device in close proximity to the household surface to determine if the microorganisms are still present.

12 Claims, No Drawings

METHOD FOR DETECTING A PLURALITY OF CATALASE POSITIVE MICROORGANISMS

BACKGROUND OF THE INVENTION

1. Field of the Invention

The present invention relates to methods and kits for detecting microorganisms on a surface by applying a cleaning composition comprising a peroxide source on a surface and using an acoustic device to detect the presence of microorganisms.

2. Description of the Related Art

Disease causing microorganisms cannot be seen or heard but they are everywhere. The spread of germs may be prevented by good hygiene practices and disinfection methods. Despite cleaning and disinfection, a germ-free environment cannot be guaranteed. The only way for a consumer to determine if a surface has been disinfected is to test the surface. Accordingly, there is a need for a consumer to determine if a surface is germ-free.

At present, there are no simple or even available tests for consumers to determine if a particular surface is disinfected. Consumers typically apply cleaning products to household surfaces and wipe the surfaces with a towel or a wipe. However, consumers do not really know if the surface has been completely disinfected. Furthermore, there are no products in the market that provide cues (i.e. audio cues) to consumers to really determine if a surface is disinfected. The present invention addresses this problem.

Advantageously, the methods and kits of the invention provide a suitable test for consumers to determine if a surface is disinfected. Consumers can simply apply a cleaning composition containing a peroxide source onto a household surface suspected of having microorganisms and then use an acoustic device to detect if a surface still contains microorganisms. Therefore, consumers will at least have an audio cue on whether the surface is disinfected.

The patent literature generally discloses that a peroxide source that comes in to contact with catalase will produce oxygen and water. However, nothing in the patent literature generally discloses that consumers can use an acoustic device (i.e. microphone) to detect if a household surface has been disinfected, thereby providing an audio cue for the consumer.

EP223479 generally discloses a method for disinfecting a medical device comprising enzymatic neutralization of a hydrogen peroxide solution. EP223479, however, fails to disclose using an acoustic device to detect if a household surface has been disinfected, thereby providing an audio cue for the consumer.

US20050283045 generally discloses a capsule medical instrument having a capsule which can be swallowed into a body cavity and an oxygen generator provided within said capsule. US20050283045 however, fails to disclose using an acoustic device to detect if a household surface has been disinfected, thereby providing an audio cue for the consumer.

US20070154466 generally discloses an implantable and insertable medical devices (also referred to herein as internal medical devices), which contain one or more peroxide-converting catalysts. US20070154466 however, fails to disclose using an acoustic device to detect if a household surface has been disinfected, thereby providing an audio cue for the consumer.

EP486653 generally discloses a method for disinfecting, moistening, and neutralizing contact lenses. EP486653 however, fails to disclose using an acoustic device to detect if a household surface has been disinfected, thereby providing an audio cue for the consumer.

SUMMARY OF THE INVENTION

In accordance with the above objects and those that will be mentioned and will become apparent below, one aspect of the present invention comprises a method for detecting a plurality of microorganisms on a household surface, said method comprising:
  a) contacting a cleaning composition comprising a hydrogen peroxide source with a household surface containing said microorganisms, wherein said microorganisms comprise a catalase; and
  b) placing an acoustic device in close proximity with said household surface to detect the presence of said microorganisms.

In accordance with the above objects and those that will be mentioned and will become apparent below, another aspect of the present invention comprises a method for detecting a plurality of aerobic microorganisms on a household surface, said method comprising:
  a) contacting a cleaning composition comprising a hydrogen peroxide source with a household surface containing said aerobic microorganisms, wherein said aerobic microorganisms comprise a catalase; and
  b) placing a unidirectional microphone within 3 inches of said household surface to detect the presence of said aerobic microorganisms.

In accordance with the above objects and those that will be mentioned and will become apparent below, another aspect of the present invention comprises a kit for detecting microorganisms on a household surface, said kit comprising:
  a) a cleaning composition comprising a hydrogen peroxide source;
  b) an acoustic device; and
  c) instructions for detecting said microorganisms wherein said instructions comprise contacting the hydrogen peroxide source with the microorganisms on the household surface and placing an acoustic device in close proximity with said household surface to detect the presence of said microorganisms.

Further features and advantages of the present invention will become apparent to those of ordinary skill in the art in view of the detailed description of preferred embodiments below, when considered together with the attached claims.

DETAILED DESCRIPTION OF THE INVENTION

Before describing the present invention in detail, it is to be understood that this invention is not limited to particularly exemplified process or kit parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The cleaning composition can be used as a disinfectant, sanitizer, and/or sterilizer. As used herein, the term "disinfect" shall mean the elimination of many or all pathogenic microorganisms on surfaces with the exception of bacterial endospores. As used herein, the term "sanitize" shall mean the reduction of contaminants in the inanimate environment to levels considered safe according to public health ordinance, or that reduces the bacterial population by significant numbers where public health requirements have not been established. And at least 99% reduction in bacterial population within a 24 hour time period is deemed "significant." As used herein, the term "sterilize" shall mean the complete elimination or destruction of all forms of microbial life and which is authorized under the applicable regulatory laws to make legal claims as a "Sterilant" or to have sterilizing properties or qualities.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone.

The term "cleaning composition", as used herein, is meant to mean and include a cleaning formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, cationic, nonionic, zwitterionic and/or amphoteric agents.

It should be noted that as used herein the term "cleaning" refers generally to a chemical, physical or enzymatic treatment resulting in the reduction or removal of unwanted material, and "cleaning composition" specifically includes, but is not limited to hard and soft surface cleaners, bleaching compositions toilet bowl cleaners, and drain openers. The cleaning composition may consist of a variety of chemically, physically or enzymatically reactive active ingredients, including solvents, acids, bases, oxidants, reducing agents, enzymes, detergents and thioorganic compounds.

The cleaning compositions of the invention may be in liquid aqueous form. They may comprise water in an amount of from 60% to 99.5% by weight, or from 80% to 99%, or from 85% to 99% by weight of the total aqueous liquid oxidant composition.

General

The present invention is directed to a method for detecting miroorganisms on a household surface. The first step of the invention is contacting a hydrogen peroxide source or a cleaning composition comprising a peroxygen source (i.e. hydrogen peroxide) with a household surface containing said microorganisms, wherein said microorganisms comprise a catalase. The second step is placing an acoustic device in close proximity with the household surface to detect the presence of the microorganisms.

In another embodiment of the present invention, a first step of the invention is contacting a cleaning composition without a peroxide source on a household surface containing said microorganisms, wherein said microorganisms comprise a catalase. The second step is contacting a peroxide source with the household surface (where the cleaning composition contacted the surface) containing said microorganisms, wherein said microorganisms comprise a catalase. The third step is placing an acoustic device in close proximity with the household surface to detect the presence of the microorganisms. Cleaning compositions that do not contain a peroxide source that could be used in this embodiment, include but are not limited to, Formula 409®, Tilex® and Pine-Sol®.

The present invention is also directed to a kit for detecting microorganisms on a household surface. The kit comprises a cleaning composition comprising a peroxygen source (i.e. hydrogen peroxide), an acoustic device and instructions which comprise contacting the peroxygen source with the microorganisms on the household surface and placing an acoustic device in close proximity with said household surface to detect the presence of the microorganisms.

Below you will find specific information that help clearly define the present invention.

Microorganisms

There are typically millions of microorganisms on household surfaces. The present invention is focused on microorganisms that contain the enzyme, catalase. Microorganisms on household surface include, but are not limited to, bacteria, fungi and yeast. Examples of bacteria that work with the present invention include, but are not limited to, *Acinetobacter, Actinobacillus, Aerococcus, Aeromonas, Azotobacter, Bacillus, Beneckea, Bordetella, Branhamella, Brucella, Chromobacterium, Citrobacter, Corynebacteria, Edwardsiella, Escherichia, Flavobacterium, Hafnia, Klebsiella, Lactobacilli, Levinea, Listeria, Moraxella, Morganella, Mycobacteria, Nectomonas, Neisseria, Pasteurella, Plesiomonas, Proteus, Pseudomonas, Salmonella, Seratia, Shigella, Staphylococcus, Veillonella, Vibrio* and *Yersinia*. Examples of fungi include, but are not limited to, *Saccharomyces, Candida* and *Aspegillus*.

The present invention typically works on "aerobic microorganisms". Aerobic microorganisms are organisms that have oxygen based metabolism. In other words, these are microorganisms that require oxygen in order to function. These microorganisms typically use oxygen to oxidize substrates (i.e., sugars and fats) in order to obtain energy (also known as cellular respiration).

Surfaces

In the present invention, the composition can be used to treat surfaces. By "surfaces", it is meant herein any household surface, institutional surface, animal surface or any auto surface. These surfaces include, but are not limited to, hard-surfaces typically found in houses like kitchens and bathrooms e.g., tiles, walls, floors, chrome, glass, smooth vinyl, any plastic, plastified wood, table top, sinks, cooker tops, dishes, sanitary fittings such as sinks, showers, shower curtains, wash basins, toilets and the like, as well as fabrics including clothes, curtains, drapes, bed linens, bath linens, table cloths, sleeping bags, tents, upholstered furniture and the like, carpets, skin, medical surfaces, industrial and institutional equipment. Exemplary embodiments of household surface also include floor surface, a kitchen surface, a toilet bowl surface, a bathroom countertop surface, a dining table surface, a kitchen sink surface, a bathroom sink surface, a bathtub surface and a shower surface. Household surfaces also include household appliances including, but not limited to, refrigerators, freezers, washing machines, automatic dryers, ovens, microwave ovens, dishwashers and so on. Other surfaces in which the present invention can be applied include, but are not limited, to the interior of an automobile, carpet, textiles, towels and sheets.

Oxidants

Oxidants, when used, include, but are not limited to, peracids, hypohalite sources, hydrogen peroxide, and/or sources of hydrogen peroxide. According to the present invention, the oxidizing agent may be an oxygen bleach, including a peroxygen, peroxyhydrate or active oxygen generating compound. Suitable peroxygen bleaches for use herein include hydrogen peroxide or sources thereof. As used herein a source of hydrogen peroxide refers to any compound which generates active oxygen when said compound is in contact with water. Suitable water-soluble sources of hydrogen peroxide for use herein include percarbonates, preformed percarboxylic acids, persilicates, persulphates, perborates, organic and inorganic peroxides and/or hydroperoxides.

In one embodiment, hydrogen peroxide is employed in the aqueous composition of the present invention. The compositions of the present invention that comprise a peroxygen bleach may further comprise a bleach activator or mixtures thereof. By "bleach activator", it is meant herein a compound which reacts with peroxygen bleach like hydrogen peroxide to form a peracid. The peracid thus formed constitutes the activated bleach. Suitable bleach activators to be used herein include those belonging to the class of esters, amides, imides, or anhydrides. Examples of suitable compounds of this type are disclosed in British Patent GB 1 586 769 and GB 2 143 231 and a method for their formation into a prilled form is described in European Published Patent Application EP-A-62 523. Suitable examples of such compounds to be used herein are tetracetyl ethylene diamine (TAED), sodium 3,5,5 trimethyl hexanoyloxybenzene sulphonate, diperoxy dodecanoic acid as described for instance in U.S. Pat. No. 4,818,425 and nonylamide of peroxyadipic acid as described for instance in U.S. Pat. No. 4,259,201 and n-nonanoyloxybenzenesulphonate (NOBS). Also suitable are N-acyl caprolactams selected from the group consisting of substituted or unsubstituted benzoyl caprolactam, octanoyl caprolactam, nonanoyl caprolactam, hexanoyl caprolactam, decanoyl caprolactam, undecenoyl caprolactam, formyl caprolactam, acetyl caprolactam, propanoyl caprolactam, butanoyl caprolactam pentanoyl caprolactam or mixtures thereof. A particular family of bleach activators of interest was disclosed in EP 624 154, and particularly preferred in that family is acetyl triethyl citrate (ATC). Acetyl triethyl citrate has the advantage that it is environmental-friendly as it eventually degrades into citric acid and alcohol. Furthermore, acetyl triethyl citrate has a good hydrolytical stability in the product upon storage and it is an efficient bleach activator. A particular family of bleach activators also of interest was disclosed in U.S. Pat. Nos. 5,741,437, 6,010,994 and 6,046,150, generally described as n-alkyl alkyl ammonium acetonitrile activators, and particularly preferred in that family is n-methyl morpholinium acetonitrile (MMA).

In addition, other classes of peroxides can be used as an alternative to hydrogen peroxide and sources thereof or in combination with hydrogen peroxide and sources thereof. Suitable classes include dialkylperoxides, diacylperoxide, performed percarboxylic acids, organic and inorganic peroxides and/or hydroperoxides. Suitable organic peroxides/hydroperoxides include diacyl and dialkyl peroxides/hydroeroxides such as dibenzoyl peroxide, t-butyl hydroperoxide, dilauroyl peroxide, dicumyl peroxide, and mixtures thereof. Suitable preformed peroxyacids for use in the compositions according to the present invention include diperoxydodecandioic acid DPDA, magnesium perphthalic acid, perlauric acid, perbenzoic acid, diperoxyazelaic acid and mixtures thereof.

Surfactants and Counterions

Where present the surfactant may be selected from anionic, nonionic, cationic, zwitterionic, amphoteric and mixtures thereof. In one embodiment of the present invention the surfactant is selected from amphoteric, zwitterionic and mixtures thereof. In another embodiment of the present invention, the surfactant is selected from amine oxide, betaine, sulphobetaine and mixtures thereof. In another embodiment of the present invention, the surfactant is selected from amine oxide, soap and mixtures thereof. The surfactant may be present in a cleaning composition from 0-50 wt %, more preferable 1-10 wt % and most preferable 1-5 wt %.

A suitable anionic surfactant is an alkali metal soap (alkyl carboxylates). The soaps utilized are typically formed in situ, by using the appropriate carboxylic acid (e.g., a $C_{6-18}$ carboxylic acid, such as, without limitation, lauric, stearic, myristic acids, and unsaturated acids, such as coco fatty acid), and neutralizing with e.g., sodium hydroxide (NaOH). Other alkali metal hydroxides, such as potassium and lithium hydroxides, can be utilized. Commercial sources of these fatty acids include Henkel Corporation's Emery Division. The soap is present in an amount of about 0.1 to 10%. In one embodiment, the soap is present in an amount of about 0.5-1.5% by weight.

Suitable anionic surfactants for use herein include alkyl sulphates. Suitable alkyl sulphates for use herein include water-soluble salts or acids of the formula $ROSO_3M$ wherein R is a C6-C24 linear or branched, saturated or unsaturated alkyl group, preferably a C8-C20 alkyl group, more preferably a C8-C16 alkyl group and most preferably a C10-C14 alkyl group, and M is H or a cation or ammonium or substituted ammonium. As discussed above, where the surfactant is used as a means of thickening the composition, suitable alkyl sulphates include those having an alkyl chain length of greater than 10 carbon atoms, or from 12 to 20 carbon atoms, or from 12 to 18 carbon atoms. Examples of suitable sulphate surfactants include sodium dodecyl sulphate, sodium tetradecyl sulphate, sodium hexadecyl sulphate. Suitable anionic surfactants for use herein further include alkoxylated sulphate surfactants. Suitable alkoxylated sulphate surfactants for use herein are according to the formula $RO(A)MSO_3M$ wherein R is an unsubstituted C6-C24 alkyl, hydroxyalkyl or alkyl aryl group, having a linear or branched C6-C24 alkyl component, or a C12-C20 alkyl or hydroxyalkyl, or C12 C18 alkyl or hydroxyalkyl, A is an ethoxy or propoxy or butoxy unit or a mixture thereof, m is greater than zero, typically between 0.5 and 6, or between 0.5 and 3, and M is H or a cation which can be, for example, a metal cation (e.g., sodium, potassium, lithium, calcium, magnesium, etc.), ammonium or substituted-ammonium cation. Alkyl ethoxylated sulphates, alkyl butoxylated sulphates as well as alkyl propoxylated sulphates are contemplated herein.

Suitable anionic surfactants for use herein further include alkyl aryl sulphates. Suitable alkyl aryl sulphates for use herein include water-soluble salts or acids of the formula $ROSO_3M$ wherein R is an aryl, for example a benzyl, substituted by a C6-C24 linear or branched saturated or unsaturated alkyl group, or a C8-C20 alkyl group, or a C10-C16 alkyl group and M is H or a cation, or ammonium or substituted ammonium.

Suitable anionic surfactants for use herein further include alkyl sulphonates. Suitable alkyl sulphonates for use herein include water-soluble salts or acids of the formula $RSO_3M$ wherein R is a C6-C20 linear or branched, saturated or unsaturated alkyl group, or a C8-C18 alkyl group, or a C14-C17 alkyl group, and M is H or a cation, e.g., an alkali metal cation or ammonium or substituted ammonium.

Suitable anionic surfactants for use herein further include alkyl aryl sulphonates. Suitable alkyl aryl sulphonates for use herein include water-soluble salts or acids of the formula $RSO_3M$ wherein R is an aryl, preferably a benzyl, substituted by a C6-C20 linear or branched saturated or unsaturated alkyl group, for example a C8-C18 alkyl group, or a C9-C14 alkyl group, and M is H or a cation, or ammonium or substituted ammonium.

Suitable anionic surfactants for use herein further include alkoxylated sulphonate surfactants. Suitable alkoxylated sulphonate surfactants for use herein are according to the formula $R(A)mSO_3M$ wherein R is an unsubstituted C6-C20 alkyl, hydroxyalkyl or alkyl aryl group, having a linear or branched C6-C20 alkyl component, or a C12-C20 alkyl or hydroxyalkyl, or a C12-C18 alkyl or hydroxyalkyl, A is an ethoxy or propoxy or butoxy unit, m is greater than zero, typically between 0.5 and 6, or between 0.5 and 3, and M is H or a cation, ammonium or substitutedammonium cation. Alkyl ethoxylated sulphonates, alkyl butoxylated sulphonates as well as alkyl propoxylated sulphonates are contemplated herein. Suitable anionic surfactants for use herein further include C6-C20 alkyl alkoxylated linear or branched diphenyl oxide disulphonate surfactants. Other suitable anionic surfactants for use herein include alkylcarboxylates.

Other anionic surfactants can include salts (including, for example, sodium, potassium, ammonium, and substituted ammonium salts such as mono-, di- and triethanolamine salts) of soap, C8-C24 olefinsulfonates, sulfonated polycarboxylic acids, acyl glycerol sulfonates, fatty oleyl glycerol sulfates, alkyl phenol ethylene oxide ether sulfates, alkyl phosphates, isethionates such as the acyl isethionates, N-acyl taurates, alkyl succinamates and sulfosuccinates, monoesters of sulfosuccinate (especially saturated and unsaturated C12-C18 monoesters) diesters of sulfosuccinate (especially saturated and unsaturated C6-C14 diesters), acyl sarcosinates, sulfates of alkyl polysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_k CH_2COO^- M^+$ wherein R is a C8-C22 alkyl, k is an integer from 0 to 10, and M is a soluble salt-forming cation.

Suitable nonionic surfactants for use herein are fatty alcohol ethoxylates and/or propoxylates, which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation.

Suitable amphoteric surfactants for use herein include amine oxides having the following formula $R^1R^2R^3NO$ wherein each of $R^1$, $R^2$ and $R^3$ is independently a saturated substituted or unsubstituted, linear or branched hydrocarbon chains of from 1 to 30 carbon atoms. Suitable amine oxide surfactants to be used according to the present invention are amine oxides having the following formula $R^1R^2R^3NO$ wherein $R^1$ is an hydrocarbon chain comprising from 1 to 30 carbon atoms, or from 6 to 20, or from 12 to 18, or from 14 to 16, and wherein $R^2$ and $R^3$ are independently substituted or unsubstituted, linear or branched hydrocarbon chains comprising from 1 to 4 carbon atoms, or from 1 to 3 carbon atoms, or are methyl groups. $R^1$ may be a saturated substituted or unsubstituted linear or branched hydrocarbon chain. $R^1$ is suitably a C16 alkyl group. Such amine oxides are commercially available from Hoechst and Clariant.

Suitable zwitterionic surfactants for use herein contain both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylates and sulfonates, although other groups like sulfates, phosphonates, and the like can be used. A generic formula for some zwitterionic surfactants to be used herein is $R^1-N(R^2)(R^3)R^4X^-$ wherein $R^1$ is a hydrophobic group; $R^2$ and $R^3$ are each C1-C4 alkyl, hydroxy alkyl or other substituted alkyl group which can also be joined to form ring structures with the N; $R^4$ is a moiety joining the cationic nitrogen atom to the hydrophilic group and is typically an alkylene, hydroxy alkylene, or polyalkoxy group containing from 1 to 10 carbon atoms; and X is the hydrophilic group which is suitably a carboxylate or sulfonate group. Suitable hydrophobic groups $R^1$ are alkyl groups containing from 1 to 24, or from 12 to 18, or from 14 to 16 carbon atoms. The hydrophobic group can contain unsaturation and/or substituents and/or linking groups such as aryl groups, amido groups, ester groups and the like. In general, the simple alkyl groups are suitable for cost and stability reasons.

Suitable zwitterionic surfactants include betaine and sulphobetaine surfactants, functionalized betaines such as acyl betaines, alkylamidoalkyldimethyl betaines, alkyl imidazoline alanine betaines, glycine betaines, derivatives thereof and mixtures thereof. Suitable betaine and sulphobetaine surfactants for use herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279, 2,255,082, and 5,252,245 incorporated herein by reference. Suitable betaine and sulphobetaine surfactants herein are according to the formula $R^2R^1-N^+-(CH_2)_n-Y-R^3$ wherein $R^1$ is a hydrocarbon chain containing from 1 to 24 carbon atoms, or from 12 to 18, or from 14 to 16, wherein $R^2$ and $R^3$ are hydrocarbon chains containing from 1 to 3 carbon atoms, or 1 carbon atom, wherein n is an integer from 1 to 10, or from 1 to 6, or is 1, Y is selected from the group consisting of carboxyl and sulfonyl radicals and wherein the sum of $R^1$, $R^2$ and $R^3$ hydrocarbon chains is from 14 to 24 carbon atoms, or mixtures thereof.

Examples of particularly suitable betaine surfactants include C12-C18 alkyl dimethyl betaine such as coconutbetaine and C10-C16 alkyl dimethyl betaine such as laurylbetaine. Coconutbetaine is commercially available from Seppic under the trade name of Amonyl 2659. Laurylbetaine is commercially available from Albright & Wilson under the trade name Empigen BB/L.

The counterion is an anionic organic counterion selected from the group consisting of $C_{2-6}$ alkyl carboxylates, aryl carboxylates, $C_{2-10}$ alkyl sulfonates, aryl sulfonates, sulfated $C_{2-10}$ alkyl alcohols, sulfated aryl alcohols, and mixtures thereof. The aryl compounds are derived from benzene or napthalene and may be substituted or not. The alkyls may be branched or straight chain, or are those having two to eight carbon atoms. The counterions may be added in acid form and converted to the anionic form in situ, or may be added in anionic form. Suitable substituents for the alkyls or aryls are $C_{1-4}$ alkyl or alkoxy groups, halogens, nitro groups, and mixtures thereof. Substituents such as hydroxy or amine groups are suitable for use with some non-hypochlorite cleaning actives, such as solvents, surfactants and enzymes. If present, a substituent may be in any position on the rings. If benzene is used, the para (4) and meta (3) positions are preferred. In some circumstances the cleaning active itself may be within the class of thickening-effective counterions. For example, some carboxylic acid cleaning actives may be present in both the acid and conjugate base forms, the latter which could serve as the counterion. The $C_{2-6}$ alkyl carboxylates may act in this manner. The counterion is added in an amount sufficient to thicken and result in a viscoelastic rheology, suitably between about 0.01 to 10 weight percent. A suitable mole ratio of betaine to counterion depends on the chain length and concentration of the betaine, type of counterion, and the ionic strength of the solution, as well as whether the primary object of the composition is phase stability or viscosity. Using CEDB and sodium xylene sulfonate (SXS), a suitable mole ratio is about 10:1 to 1:3, or about 2:1 to 1:2. A suitable weight ratio of CEDB to SXS is about 15:1 to 1:2, or 3:1 to 1:1.

Optional Ingredients

The pH of the cleaning composition according to the present invention, as is, is typically from 2 to 14, or from 7 to 13. The liquid compositions of the invention have a pH of from 7.5 to 13, or from 8 to 12, or from 8.5 to 11.5, when diluted into 1 to 500 times its weight of water. Optionally, the pH range is suitably provided by the pH buffering component if present. However, in addition to these components, a strong source of alkalinity may also optionally be used.

Suitable sources of alkalinity are the caustic alkalis such as sodium hydroxide, potassium hydroxide and/or lithium hydroxide, and/or the alkali metal oxides such as sodium and/or potassium oxide. A suitable strong source of alkalinity is a caustic alkali, for example sodium hydroxide and/or potassium hydroxide. Typical levels of such caustic alkalis, when present, are of from 0.1% to 1.5% by weight, or from 0.5% to 1.5% by weight of the composition.

The compositions according to the present invention may optionally comprise a pH buffering component or mixture thereof. The pH buffering component ensures that the pH of the composition is buffered to a pH value ranging from 7.5 to 13, or from 8 to 12, or from 8.5 to 11.5 after the composition has been diluted into 1 to 500 times its weight of water. Suitable pH buffering components for use herein are selected from the group consisting of alkali metal salts of carbonates, polycarbonates, sesquicarbonates, silicates, polysilicates, boron salts, phosphates, stannates, alluminates and mixtures thereof. Suitable alkali metal salts for use herein are sodium and potassium.

Suitable pH buffering components are selected from the group consisting of sodium carbonate, sodium silicate, sodium borate, sodium metaborate and mixtures thereof. Liquid oxidant compositions herein preferably contain an amount of pH buffering component of from 0.5% to 9% by weight, or from 0.5% to 5% by weight, or from 0.6% to 3% by weight of the composition.

Suitable radical scavengers for use herein include aromatic radical scavengers comprising an unsaturated ring system of from 3 to 20 carbon atoms, or from 3 to 18, or from 5 to 14 and having a double bond set comprising a total of 4n+2 electrons, wherein n is an integer of from 0 to 4, preferably of from 1 to 3. Indeed said aromatic radical scavengers include benzene derivatives, naphthalene derivatives, annulene derivatives, cyclopentadiene derivatives, cyclopropene derivatives and the like, especially aryl carboxylates and/or aryl sulfonates. Further aromatic radical scavengers include but are not limited to, substituted diarylamines, p-phenylenediamines, substituted dihydroquinolines, napthylamines, and mixtures thereof.

The cleaning composition according to the invention may comprise other optional components such as pH buffering components, stabilizing agents, other oxidant-stable surfactants, builders, fragrances, coloring agents, whiteners, solvents, soil release polymers, bacteriocidal agents, chelating agents, thickening agents, polymers, dyes, solvents, perfumes, brighteners, and mixtures thereof. Suitable chelating agents include, but are not limited to, phosphonate and aminophosphonate. In a preferred embodiment, the wt % of chelating agents in a cleaning composition is between 0.02-5 wt %.

Water

It should be briefly noted that the main ingredient of the oxidizing compositions disclosed herein is water, preferably softened, distilled or deionized water. Water provides the continuous liquid phase into which the other ingredients are added to be dissolved/dispersed. The amount of water present generally exceeds 30% and can be as high as 99.9%, although generally, it is present in a quantity sufficient (q.s.) to provide the appropriate rheology characteristics desired.

Catalase

The present invention utilizes catalase found in microorganisms. Catalase is an enzyme found in most living organisms, including many microorganisms. Catalase catalyzes the decomposition of hydrogen peroxide to oxygen and water. In fact, one catalase molecule can catalyze millions of molecules of hydrogen peroxide to oxygen and water per second. The reaction of the decomposition of the hydrogen peroxide is shown below:

$$2 H_2O_2 \rightarrow 2H_2O + O_2.$$

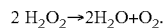

The decompositon of hydrogen peroxide is only possible by viable organisms and the release of oxygen could be visualized in the form of gaseous bubbles. Catalase is a tetramer of four polypeptide chains, each over 500 amino acids long. The enzyme, catalase, contains four porphyrin heme (iron) groups that allow the enzyme to react with the hydrogen peroxide. The optimum pH for catalase is about 7.5 but can vary depending by species. Catalysis works at an optimum temperature of 37° C. but can function at varying temperature depending upon the species. In microbiology, the catalase test is used to differentiate between specific species. A cleaning composition comprising a hydrogen peroxide source is contacted with surface with microorganisms containing the catalase. If the surface containing the microorganisms bubbles or froth forms (oxygen being released), the organism is said to be catalase-positive; if not, the organism is catalase-negative. This test is particularly useful in distinguishing staphylococci and micrococci, which are catalase-positive, from streptococci and enterococci, which are catalase-negative. Catalase can also oxidize different toxins, such as formaldehyde, formic acid, and alcohols. Catalase is usually located in a cellular organelle called the peroxisome. Hydrogen peroxide is used as a potent antimicrobial agent when cells are infected with a pathogen. Pathogens that are catalase-positive, including, but not limited to, *Mycobacterium tuberculosis, Legionella pneumophila*, and *Campylobacter jejuni*. Catalase can be generally found in many bacteria and fungi. In general, catalase may be found in aerobic microorganisms and generally not found in anaerobic organisms. Notable exceptions include, but are not limited to, *Streptococcus* species (aerobic bacteria that do not possess catalase) and *Methanosarcina barkeri*

(anaerobic bacteria that possess catalase). In another embodiment, the present invention utilizes enzymes selected from the group consisting of peroxidases and hydroperoxidases which are found in microorganism. Similar to catalase, these enzymes break down hydrogen peroxide source to water and oxygen.

Acoustic Device

The present invention also comprises an acoustic device. An acoustic device is a device that amplifies or transmits sound. In a preferred embodiment, the acoustic device is a microphone. A microphone is an acoustic device that converts or transmits sound waves in the air to an electrical signal (measured in millivolts). The most common method of coverting sound waves to an electric signal is via a thin membrane producing some proportional electrical signal. Most microphones in use today for audio use capacitance change (condenser microphones), electromagnetic generation (dynamic microphones) or piezoelectric generation to produce the signal from mechanical vibration.

Suitable condenser microphones perform when one or more diaphragm(s) acts as one plate of the capacitor and the vibrations produce changes in the distance between the plates. Condensor microphone requires a power source, provided from microphone inputs known as phantom power or from a small battery power. Power is necessary for establishing the capacitor plate voltage, and is also needed for internal amplification of the signal to a useful output level. In another embodiment, the condenser microphone can be an electret condenser microphone. The electret is a ferroelectric material that has been permanently electrically charged or polarized. The electret condenser microphone does not require polarizing voltage, but normally contain an integrated preamplifier which does require power.

Suitable dynamic microphones work via electromagnetic induction. There are generally two types of dynamic microphones: moving coil microphone and ribbon microphone. In the moving coil microphone, a small movable induction coil, positioned in the magnetic field of a permanent magnet, is attached to the diaphragm. When sound enters through the windscreen of the microphone, the sound wave moves the diaphragm. When the diaphragm vibrates, the coil moves in the magnetic field, producing a varying current in the coil through electromagnetic induction. In ribbon microphones, a thin, usually corrugated metal ribbon is suspended in a magnetic field. The ribbon is electrically connected to the microphone's output, and its vibration within the magnetic field generates the electrical signal.

Suitable piezoelectric microphones (i.e. crystal microphone) contain some materials that produce voltage when subjected to pressure, convert vibrations into an electrical signal. In a preferred embodiment, the material is Rochelle salt (potassium sodium tartrate), which is a piezoelectric crystal that works as a transducer, both as a microphone and as a slimline loudspeaker component.

A microphone's directionality or polar pattern indicates how sensitive it is to sounds arriving at different angles about its central axis. In one embodiment, the microphone is a unidirectional microphone in which it is sensitive to sounds from only one direction. In a more preferred embodiment, the unidirectional microphone is a cardioid microphone because the sensitivity pattern is heart-shaped. In another embodiment, the microphone is bidirectional meaning it can receive sound from the front and back of element. In another embodiment, the microphone is omnidirectional microphone in which it is sensitive to sounds from all directions. The smallest diameter microphone will give the best omnidirectional characteristics at high frequencies. In another embodiment, the microphone is bidirectional meaning it can receive sound from the front and back of element.

Other types of microphones that can be used with the present invention, include, but are not limited to, a lavalier microphone (hands-free microphone), a wireless microphone, a contact microphone (i.e. pick up vibrations directly from the object as opposed to sound vibrations carried through the air), and a parabolic microphone (uses a parabolic reflector to collect and focus sound waves onto a microphone receiver).

The acoustic device (i.e. microphone) can be placed in close proximity to the microorganisms on the surface. The proximity is determined by the sensitivity and sophistication of the acoustic device. In one embodiment, an acoustic device may be placed within 1, 2, 3, 4, 5, 6, 7, 8, 9, 10 or 11 inches of the surface. In another embodiment, an acoustic device may be placed within 1 foot, 2 feet, 3 feet, 4 feet or 5 feet feet away from the surface. As discussed above, the acoustic device will detect the reaction of the peroxide source with the catalase located inside the microorganisms, thereby giving off oxygen (in bubble form) and water. When a bubble is formed, energy is trapped in it. After formation, the bubble emits a sinusoidal sound that decays as energy and is dissipated from the bubble. By placing a highly sensitive microphone next to the reaction mixture, the formation and burst of the bubbles could be amplified and can be heard acoustically. The rate and amount of bubble formation is directly proportional to the number of viable organisms.

The sensitivity of an acoustic device (i.e., a microphone) is determined by how much electrical output a microphone produces for a certain sound pressure input (i.e. db SPL). The term "db SPL" is a measurement of Sound Pressure Level (SPL) which is the force that acoustical sound waves apply to air particles. Therefore, the SPL is loudest when one is near a sound source and is weakest as one moves away from the sound source. As reference, 0 db SPL is the quiestest sound a human ear can hear. Additionally, 1 db SPL is the smallest change in level a human ear can detect. It is quite known in the acoustics field that a human speaking 3 feet away is about 60 db SPL while a jackhammer 3 feet away is about 120 db SPL. The concentration of bacteria on a household surface is directly proportional to the sound pressure input. Therefore, a lower concentration of bacteria on a household surface would elicit a lower dB SPL.

In the present invention, the acoustic device can pick up different ranges of sound levels. In one embodiment, the acoustic device can pick up between 5 and 50 dB SPL. In another embodiment, the acoustic device can pick up between 10 and 40 dB SPL. In another embodiment, the acoustic device can pick between 15 and 30 dB SPL. In another embodiment, the acoustic device can pick between 20 and 30 db SPL. In another embodiment, the acoustic device can pick up 20 db SPL. In another embodiment, the acoustic device can pick up 30 dB SPL. In another embodiment, the acoustic device can pick up 40 dB SPL.

Optional

Optionally, a swab may be used with the method and kit of the present invention. The swab will be used to contact the hydrogen peroxide source with the surface containing the microorganisms. In a preferred embodiment, the swab is a cotton swab. A swab may be attached to be a stick or stiff wire for better access.

Optionally, a filter disk may be used with the present invention. In one embodiment, a filter disk contacts the surface containing the microorganisms. The filter disk is dropped into a solution comprising the hydrogen peroxide source. If there are viable microorganisms containing catalase on the filter disk, the oxygen gas will quickly bring the filter disk back up to the surface. If there are no viable microorganisms containing catalase on the filter disk, the disk will sink to the ground.

EXAMPLES

Example 1

Materials
1. Hydrogen Peroxide, 37%
2. *Staphylococcus aureus* grown overnight on Trypticase soy agar
3. 12×75 mm Glass Test Tubes
4. Microscope Slide
5. Inoculating Loop
6. NEC Microphone
7. Pasteur Pipette or Dropper The following is an example of the current invention. With an inoculating loop, pick the center of a 18-25 hour colony from an agar plate and place the center on either a clean glass slide or a 12×75 mm test tube. Prepare an identical set (using a glass slide or test tube). To one set, add a drop of water over the microorganism on the glass slide or 0.5 ml of water into a test tube with Pasteur Pipette (label as control). Repeat the same with the other set but replace water with disinfecting solution (i.e. Clorox 409®). Label this set as "Test". Add a drop of hydrogen peroxide to the glass slide or 1.0 ml into the test tube with Pasteur Pipette to both test and control. Observe for immediate bubbling (liberation of oxygen gas) from control set but not from test samples. Place microphone within 3 inches of the reaction mixture and listen to the formation and burst of bubbles acoustically. The lack of noise from test samples indicates the absence of viable microorganisms in sample exposed to disinfecting agent.

Example 2

Sample Cleaning Formulations to be Used with Current Invention

| Formulation A | |
|---|---|
| Ingredient | Wt % |
| Nonionic Surfactant (Neodol) | 2-4 |
| Fluorescent Whitener distyrylbiphenyl-stillbene | 0.1-0.7<br>0.01-0.3 |
| Blue Dye (Anthroquinone) | 0.0002-0.001 |
| Fragrance | 0.01-0.05 |
| Hydrogen Peroxide | 3-7 |
| Aminopolyphosphonate Chelating Agent | 0.06-0.25 |
| Free Radical Scavenger | 0.005-0.02 |
| Phosphoric Acid | sufficient to adjust pH to 2.3 |
| Deionized Water | Balance |

| Formulation B | |
|---|---|
| Ingredient | Wt % |
| Hydrogen Peroxide | 3.5 |
| Brightner[1] | 0.16 |
| Dye[2] | 0.0005 |
| Surfactant[3] | 3.5 |
| Fragrance | 0.01 |
| Free Radical Scavanger | 0.01 |
| Chelating Agent | 0.12 |
| pH Adjusting Agent ($H_3PO_4$) | 0.1 |
| Water | Balance |

[1]Fluorescent Whitening Agent, a distyryl biphenyl compound, e.g. Tinopal CBS-X. from Ciba-Geigy, Inc.
[2]Anthraquinone dye, Acid Blue 25, from Sandoz Company
[3]Surfactant was Neodol 25-7, a $C_{12\text{-}15}$ linear ethoxylated alcohol with about 7 moles of ethylene oxide per mole or alcohol.

| Formulation C | |
|---|---|
| Ingredient | Wt % |
| Hydrogen Peroxide | 4.0 |
| Whitener (Distyrylbiphenyl) | 0.3 |
| Acid Blue Dye | 0.001 |
| Surfactant (Triton X-100) | 4.0 |
| Chelating Agent (Aminopolyphosphonate) | 0.18 |
| pH Adjusting Agent (Sulfuric Acid) | 0.035 |
| Free Radical Scavenging Agent | 0.01 |
| Water | Balance |

| Formulation D | |
|---|---|
| Ingredient | Wt % |
| Hydrogen Peroxide | 3.0 |
| Whitener (Phorwite CNA) | 0.3 |
| Acid Blue Dye | 0.001 |
| Surfactant (Neodol 25-9) | 3.0 |
| Chelating Agent (Aminopolyphosphonate) | 0.2 |
| pH Adjusting Agent (Sulfuric Acid) | 0.035 |
| Free Radical Scavenging Agent | 0.01 |
| Water | Balance |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:
1. A method for detecting a plurality of catalase-positive microorganisms on a household surface, said method comprising:
    a) contacting a cleaning composition comprising a hydrogen peroxide source with a household surface containing said plurality of catalase-positive microorganisms;
    b) placing an acoustic device in close proximity with said household surface;
    c) monitoring the presence of sound and sound intensity through the acoustic device; and
    d) detecting a plurality of catalase-positive microorganisms on said household surface, wherein the intensity of the sound correlates to the number of catalase-positive microorganisms on said household surface.

2. The method of claim 1, wherein said microorganisms are selected from bacteria, and fungi.

3. The method of claim 1, wherein said household surface is selected from a floor surface, a kitchen surface, a toilet bowl surface, a bathroom countertop surface, a dining table surface, a kitchen sink surface, a bathroom sink surface, a bathtub surface and a shower surface.

4. The method of claim 1, wherein said cleaning composition comprises
   a) 0.05-50 wt % of an peroxygen component;
   b) 0-50 wt % of at least one surfactant; and
   c) 0.0002-1 wt % of a dye.

5. The method of claim 1, wherein said acoustic device is a microphone.

6. The method of claim 1, wherein said acoustic device is placed within 3 inches with said household surface.

7. The method of claim 1, wherein said acoustic device is placed within 1 foot with said household surface.

8. The method of claim 1, wherein said acoustic device is placed within 3 feet with said household surface.

9. The method of claim 1, wherein said acoustic device can pick up between 5 and 50 dB Sound Pressure Level ("dB SPL") from said microorganisms on said household surface.

10. The method of claim 1, wherein said acoustic device can pick up between 10 and 40 dB SPL from said microorganisms on said household surface.

11. The method of claim 1, wherein said acoustic device can pick up between 15 and 30 dB SPL from said microorganisms on said household surface.

12. A method for detecting a plurality of catalase-positive microorganisms on a household surface, said method comprising:
   a) contacting a cleaning composition without a hydrogen peroxide source with a household surface containing said plurality of catalase-positive microorganisms;
   b) contacting a hydrogen peroxide source with the household surface at the same location where the cleaning composition was applied to the household surface;
   c) placing an acoustic device in close proximity with said household surface;
   d) monitoring the presence of sound and sound intensity through the acoustic device; and
   e) detecting a plurality of catalase-positive microorganisms on said household surface, wherein the intensity of the sound correlates to the number of catalase-positive microorganisms on said household surface.

* * * * *